US007841880B2

(12) United States Patent
Ikeda

(10) Patent No.: US 7,841,880 B2
(45) Date of Patent: Nov. 30, 2010

(54) ENDOSCOPE CONNECTOR USING WATERPROOF CAP

(75) Inventor: Toshiyuki Ikeda, Saitama (JP)

(73) Assignee: Fujifilm Corporation, Tokyo (JP)

( * ) Notice: Subject to any disclaimer, the term of this patent is extended or adjusted under 35 U.S.C. 154(b) by 0 days.

(21) Appl. No.: 12/466,642

(22) Filed: May 15, 2009

(65) Prior Publication Data

US 2009/0286412 A1  Nov. 19, 2009

(30) Foreign Application Priority Data

May 16, 2008 (JP) ............................. 2008-130104
May 16, 2008 (JP) ............................. 2008-130105
May 16, 2008 (JP) ............................. 2008-130106

(51) Int. Cl.
*H01R 13/52* (2006.01)

(52) U.S. Cl. ...................................... 439/271

(58) Field of Classification Search ................. 439/271, 439/283, 294, 292, 287, 272
See application file for complete search history.

(56) References Cited

U.S. PATENT DOCUMENTS 3,489,987 A * 1/1970 Niskin .......................... 439/287
4,820,181 A * 4/1989 Kuzuno et al. ............... 439/272

FOREIGN PATENT DOCUMENTS

| JP | 6-133919 A | 5/1994 |
| JP | 9-327434 A | 12/1997 |
| JP | 2000-340290 A | 12/2000 |
| JP | 2001-204681 A | 7/2001 |
| JP | 2005-192772 A | 7/2005 |
| JP | 2005-261837 A | 9/2005 |
| JP | 2005-278944 A | 10/2005 |

* cited by examiner

*Primary Examiner*—Javaid Nasri
(74) *Attorney, Agent, or Firm*—Birch, Stewart, Kolasch & Birch, LLP

(57) ABSTRACT

A connector for an endoscope mounting a waterproof cap on a connection port for a connector having electrical connection member disposed therein in which an O ring providing waterproof characteristics by making close contact with an inner periphery of the connection port and a second seal member providing waterproof characteristics by making close contact with a front face of a rotating ring used for fixing a connector receiving part disposed on an outer periphery of the connection port are provided. The second seal member has a size which does not exceed the outer periphery of the rotating ring due to being formed in a bell shape having a flared section. A third seal member (O ring, V ring or oil seal) maintaining a watertight condition is provided between the rear end of the rotating ring and the rear member of the main body of the connector.

6 Claims, 6 Drawing Sheets

ENDOSCOPE CONNECTOR USING WATERPROOF CAP

BACKGROUND OF THE INVENTION

The disclosure of Japanese Patent Applications Nos. 2008-130104, 2008-130105 and 2008-130106, filed on May 16, 2008, including its specification, claims and drawings, is incorporated herein by reference in its entirety.

1. Field of the Invention

The present invention relates to a connector for an endoscope for connecting the endoscope to a processor device or the like. In particular, the present invention relates to the prevention of corrosion of electrical connection members using a waterproof cap.

2. Description of the Related Art

FIG. 10 shows the structure of a conventional endoscopic connector (electrical connector). In FIG. 10, a waterproof cap 2 is shown as mounted on a connector 1. The connector 1 is mounted on an outer periphery of a main body 3 having a rotating (operating) ring 4 rotatable through a predetermined angle. A plurality of pins (electrical connection members) 5 is disposed in an inner section of a connection port 3a of the main body 3. The waterproof cap 2 includes an inner cylindrical section 6 and an outer cylindrical section 7. An O ring 8 is mounted in a groove 6e of an outer periphery of the inner cylindrical section 6 and makes close contact with an inner periphery of the connection port 3a.

A bayonet method for example is used in this type of connector for endoscope as a method of connecting and fixing to a connector receiving part on the processor device. This bayonet structure can also be used for connection and affixation with the waterproof cap 2. For example, an engagement hook 9 is provided at two or three positions on an outer distal periphery of the outer cylindrical section 7 and is disposed in and engaged with a cam groove formed on an inner periphery of the rotating ring 4. In this manner, the waterproof cap 2 can be connected and fixed to the connector 1 by engaging the engagement hook 9 with the cam groove of the rotating ring 4 and pressing in the waterproof cap 2 by rotating through a predetermined angle.

FIG. 11 shows the structure of the connector 1 and the connector receiving part on the processor device 10. In the same manner as the engagement hook 9 for the waterproof cap 2, an engagement hook 12 is provided on the connector receiving part (receptacle) 11 of the processor device 10. Thus in a conventional connector 1, by aligning a mark (reference) $M_1$ provided on an outer periphery of the rotating ring 4 to a mark $M_2$ on the processor device 10, the connector receiving part 11 is inserted into the rotating ring 4 and the cam groove is engaged with the engagement hook 12. Then the rotating ring 4 is rotated to the mark $M_3$ and the connector main body 3 (the connection port 3a thereof) is displaced forward and connected and fixed to the connector receiving part 11. When the connector 1 is removed from the connector receiving part 11, the rotating ring 4 is returned to an original reference position by the resilient force of a spring.

In this type of connector for endoscope, if the waterproof cap 2 is mounted on the connector 1 when removed from the connector receiving part 11, waterproofing and maintenance of watertight conditions are enabled in an inner section of the connector 1 which has pins 5 acting as electrical connections since the O ring 8 of the waterproof cap 2 makes close contact with the inner peripheral face of the connection port 3a. Thus washing or sterilization such as autoclaving of the endoscope (scope) can be performed with the connector 1 in a waterproof state.

SUMMARY OF THE INVENTION

However although the conventional connector for an endoscope described in FIG. 10 is adapted to be waterproof by close contact of the O ring 8 of the cap 2 with the inner peripheral face of the connector port 3a, since the rotating ring 4 is provided on an outer peripheral side of the connection port 3a, when moisture enters and becomes adhered to the space between the rotating ring 4 and the main body 3, if the waterproof cap 2 is removed from the connector 1, moisture adhering to the space (or accumulated therein) drips into and enters the inner section of the connection port 3a which has the pins 5. Consequently when the connector 1 which contains moisture is connected with the connector receiving part 11, the inner section of the connector receiving part 11 will also be wetted with moisture and as a result the electrical connections in the connector receiving part 11 in addition to the pins 5 in the connector 1 may corrode.

Furthermore the rotating ring 4 may be omitted and a simple outer covering body which does not rotate to the position of the rotating ring 4 may be provided on an outer periphery of the connection port 3a. However the same problem arises with this arrangement since moisture adheres to any space between the outer covering body and the main body 3.

In the prior art, Patent Document 1 (Japanese Patent Application Publication No. JP-A-6-133919) and Patent Document 2 (Japanese Patent Application Publication No. JP-A-2000-340290) are examples of removing moisture which has entered a connector. Patent Document 1 discloses a mechanism for prevention of water leakage onto the electrical connections in a plug by disposing a sponge in a plug of the endoscopic device and engaging the plug to a socket. Moisture adhering to the plug is absorbed by the sponge. Patent Document 2 discloses an arrangement in which a water removal cover is provided in the connector. The cover is provided with holes enabling insertion and close liquid-tight contact with the electrical connecting members. The water removal cover is displaced in order to remove moisture adhering to the proximity of the electrical connection members.

However when the water absorption capacity of the sponge is exceeded in Patent Document 1, water entry occurs and there is the possibility of corrosion to electrical connections. Since a user must operate the moisture removal cover in Patent Document 2, when the removal operation is forgotten, moisture cannot be completely removed and there remains the possibility of corrosion to electrical connection members.

Furthermore a seal for the connector may be provided as shown in Patent Document 3 (Japanese Patent Application Publication No. JP-A-2005-278944). Patent Document 3 seals the electrical connection section in the connector by creating a seal by connecting connectors disposed at both ends of a junction cable. However in Patent Document 3, when the connection of the connectors is released, moisture adhering to the connection section falls into the inner section of each connector and causes the possibility of corrosion of electrical connection sections similar to the other prior art documents.

As shown by Patent Document 4 (Japanese Patent Application Publication No. JP-A-2001-204681), a space between a base of a connection tube for an electrical connector and an outer cap member for a waterproof cap is sealed with a first seal member and a space between an open section of a connection tube and an inner cap member is sealed with a second seal member. Therefore the effect of sealing is increased by both the inner side and outer side of a connection tube of an electrical connector. However this arrangement uses a largesized waterproof cap which increases the outer periphery of the electrical connector when the waterproof cap is attached.

In addition, metallic members are used in supporting sections in waterproof caps used in conventional electrical connectors and each of these members is connected and fixed. As a result, the problem arises that when metallic screws and adhesives are used, the adhesive effect deteriorates due to deterioration of the adhesive or corrosion of the metallic sections of the waterproof cap. In other words, corrosion and deterioration of adhesives tends to occur when an endoscope undergoes sterilization such as washing, disinfection or autoclaving and when placed in high temperature and high humidity and immersed in strong acidic water.

For example, Patent Document 4 above in which a waterproof cap is provided for an electrical connector discloses that the cap member is fixed to a guide tube with a screw and the cap member may be formed from metallic material. However the above problems result.

As shown by Patent Document 5 (Japanese Patent Application Publication No. JP-A-2005-192772), a covering cap is formed from a resilient rubber material which is easily held even when the cap reaches a certain temperature and which enables omission of an O ring. However in Patent Document 5, since the rubber member forming the covering cap performs the role of an O ring (seal member), when the rubber of the sealing section deteriorates, the entire waterproof cap must be exchanged and thus produces undesirable results with respect to components and costs.

The present invention is proposed in light of the above problems and according to a first aspect of the present invention, a connector for an endoscope is provided in which moisture adhering to a space between a main body having a connection port and an outer covering body or rotating ring disposed on an outer side of the main body does not enter into the connector when removing a waterproof cap and which ensures prevention of corrosion of the electrical connection members. Furthermore even when the waterproof cap is attached, the outer periphery of the connector is not increased.

In addition to the first aspect, in a connector for an endoscope according to a second aspect, the outer periphery of the connector is not increased when the waterproof cap is attached.

In addition to the first aspect, a connector for an endoscope according to a third aspect enables prevention of corrosion of the waterproof cap and deterioration of adhesives by avoiding use of metals or adhesives.

In order to achieve the first aspect, the present invention provides a connector for an endoscope provided with a connection port for a connector having an electrical connection member disposed therein and an outer member disposed on an outer periphery of the connection port, and having a waterproof cap mounted thereon. The waterproof cap has a first seal member which provides waterproof characteristics by making close contact with the inner peripheral face of the connection port and a second seal member which provides waterproof characteristics by making close contact with the front face (front end face) of the outer member.

The structure of the invention is such that the first seal member which makes close contact with the inner peripheral face of the connection port of the connector prevents entry of moisture into the connection port. Furthermore the second seal member which makes close contact with the front face of a connection port outer member (for example, the outer covering body) prevents moisture from adhering (or accumulating in) in the space between the outer member and the connector main body and thus prevents leakage of moisture onto the electrical connection members in the connection port.

A rotating ring is provided as the outer member and is disposed to rotate on an outer side of the connection port and is rotated in order to fix the connector to the connector receiving part. A third seal member is provided between the rear end of the rotating ring and the connector main body in order to maintain watertight characteristics and thus the second seal member of the waterproof cap can be disposed in close contact with the front face of the rotating ring. In this manner, the second seal member which is in close contact with the front face for example of the rotating ring prevents moisture from entering from the front side into the space between the rotating ring and the connector main body. The third seal member which is disposed between the rear end of the rotating ring and the connector main body prevents moisture from entering therebetween from the rear side. Therefore moisture does not adhere to (or accumulate in) the space between the rotating ring and the connector main body.

Furthermore when attaching the waterproof cap to the connector, a forward fixing mechanism (such as a bayonet type or threadably engaged type) is provided to enable connection and affixation to the connector while displacing the waterproof cap forward. The forward motion operation of the forward fixing mechanism enables the second seal member to press onto the front face of the connector outer member. With this type of arrangement, the second seal member is pressed firmly onto the front face of the connector outer member by the forward operation of the forward fixing mechanism which uses a bayonet type or threadably engaged type fixing mechanism.

The connector for an endoscope according to the present invention has the effect of ensuring prevention of corrosion to electrical connection members in addition to preventing entry of moisture adhering in the space between main body provided with a connection port and the rotating ring disposed an outer side thereof or a member such as an outer covering body.

In order to achieve the second aspect, another (second) invention provides a connector for an endoscope provided with a connection port for a connector having electrical connection members disposed therein and an outer member disposed on an outer side of the connection port, and having a waterproof cap mounted thereon. The waterproof cap is provided with a first seal member which provides waterproof characteristics by making close contact with the inner peripheral face of the connection port and a second seal member which is formed from a seal body which is not larger than the outer periphery of the outer member and which provides waterproof characteristics by making close contact with the outer member.

In this further invention, in addition to the first seal member, the second seal member which makes close contact with the outer member of the connection port prevents moisture from adhering to the space between the outer member and the connector main body and also prevents moisture from wetting the electrical connection members in the connection port. A further effect is obtained that even when the waterproof cap is attached, the outer periphery of the connector is not increased which facilitates handling during sterilization operations such as washing, disinfecting and autoclaving and the waterproof cap itself as well as the connector with the waterproof cap attached is slender and compact.

In order to achieve the third aspect, another (third) invention provides a connector for an endoscope provided with a connection port for a connector having an electrical connection member disposed therein and having a waterproof cap mounted thereon. A waterproof seal member for the connector formed from resilient rubber and a first member and a second member are provided. The first member and second member are formed from a synthetic resin material, are constituted by at least two members forming the waterproof cap (main body) by connection via press fitting and form a space into which the base of the seal member above is sandwiched during press fitting and connection. The seal member above is mounted on the waterproof cap by press fitting and connection with the first member and second member by sandwiching the seal member between the first member and second member.

According to this further invention, the seal member is mounted by press fitting and connection with the first member and the second member. The formation of the whole waterproof cap from synthetic resin material and resilient rubber facilitates the manufacture of the waterproof cap without the use of metallic materials, metallic screws and adhesives.

In this further invention, a first seal member which produces waterproofing effects by close contact with the inner peripheral face of the connection port and a second seal member which produces waterproofing effects by close contact with the outer member disposed on an outer side of the connection port are provided. Thus the second seal member can be mounted between the first member and the second member. In this manner, entry of moisture into the connection port can be prevented by the first seal member which makes close contact with the inner peripheral face of the connection port of the connector. In addition, the second seal member which makes close contact with the outer member of the connection port (for example, the outer covering body) prevents moisture from adhering to (or accumulating in) a space for example between the outer member and the connector main body and thus prevents moisture from wetting the electrical connection members in the connection port.

The manufacture of the waterproof cap without use of metal or adhesives in a connector for an endoscope according to this further invention ensures prevention of corrosion to the waterproof cap and prevents deterioration of an adhesive effect due to deterioration of an adhesive. Furthermore, for example, assembly and manufacture of the waterproof cap is facilitated since the second seal member is mounted using a press-fitting connection with the first member and the second member.

DETAILED DESCRIPTION OF THE PREFERRED EMBODIMENTS

Figure 1:
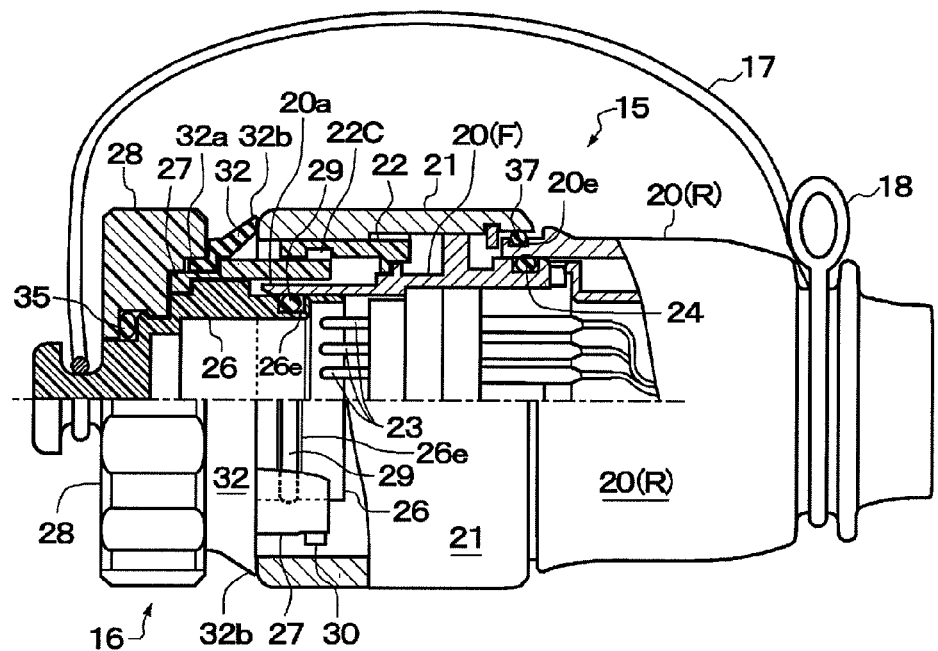
FIG. 1 is a partial sectional view showing the structure of an endoscopic connector (shown with a waterproof cap mounted) according to a first embodiment of the present invention.
Figure 2:
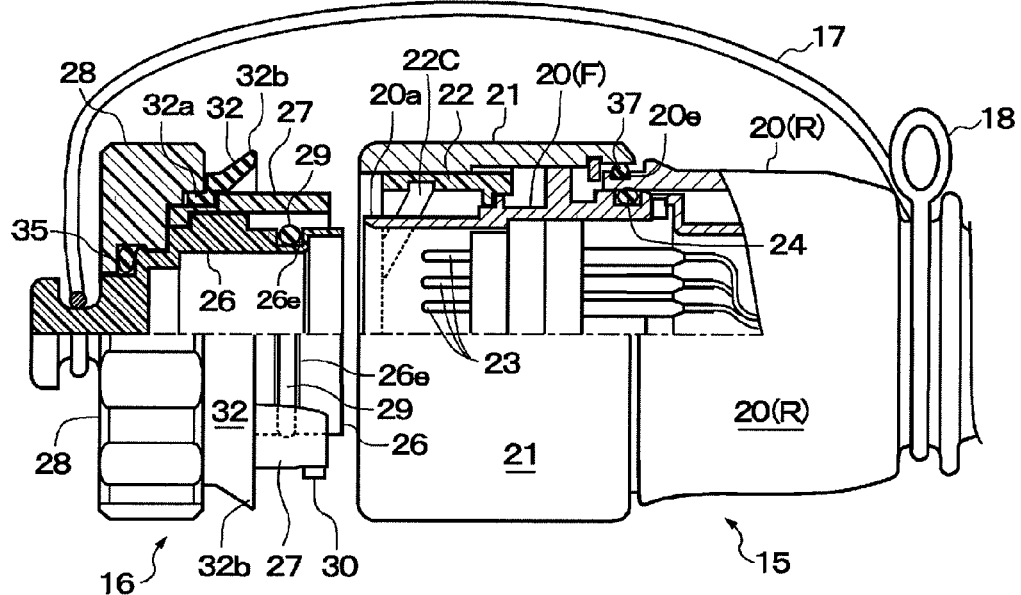
FIG. 2 is a partial sectional view showing the structure of a connector for an endoscope (shown with a waterproof cap mounted) according to the first embodiment of the present invention.

FIGS. 1 to 6 show the structure of a connector for an endoscope according to a first embodiment. In the first embodiment, as shown in FIG. 1 and FIG. 2, a waterproof cap 16 is mounted on a connector 15. The waterproof cap 16 is connected by a string-like body 17 to the cable side of the connector 15 and a ring-shaped (or hook-shaped) engagement member 18 is provided on the base of the connector side of the string-shaped body 17. The engagement member 18 is used to engage the connector 15 to other members, for example to the optical connector section. In other words, the connector 15 which acts as an electrical connector is provided on the endoscope side and is connected to a signal processing circuit section such as a processor device. For example, the connector 15 is provided on the end of the cable branching from the optical connector of the endoscope connected to the light source (for example, refer to Japanese Patent Application Publication No. JP-A-2005-261837) and thus is difficult to store when not in use. Consequently in a first embodiment, the engagement member 18 is used to engage the connector 15 to a member such as the optical connector in order to facilitate storage.

Figure 3:
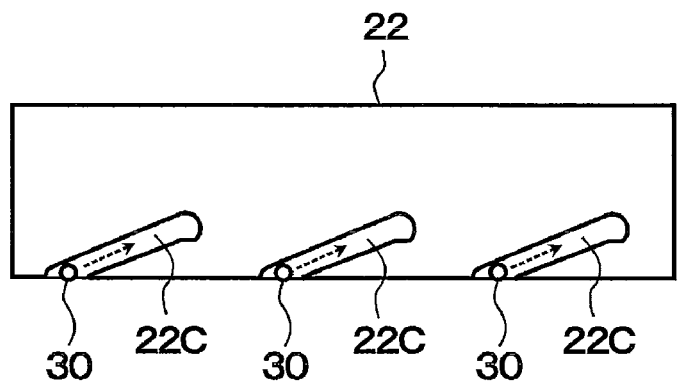
FIG. 3 is an expansion plan view of a cylindrical member showing the structure of the cam groove in this embodiment.

The connector 15 employs a bayonet method (forward fixing mechanism) as a method of connecting and fixing to the waterproof cap 16 and the connector receiving part on the processor device. Due to the bayonet connection, a rotating (operating) ring 21 is rotatably disposed on the outer periphery of a main body 20 and a resilient force is applied to the rotating ring 21 from the main body 20 to return to a reference position (position prior to mounting). As shown in FIGS. 1-3, two or three cam grooves (inclined grooves) 22C are formed on an inner peripheral face of the rotating ring 21. The grooves 22C are engaged to two or three engagement hooks 12 (e. g., shown in FIG. 11B) provided on a connector receiving part (receptacle) ii of the processor device i0 and displace the connector 15 slightly in a forward direction.

Figure 11A:
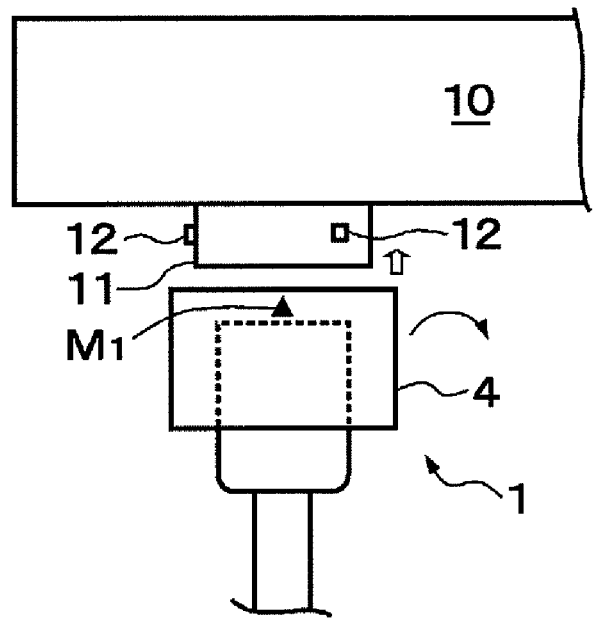
FIG. 11A is an upper view of a connector receiving part in a processor device and a connector for an endoscope.
Figure 11B:
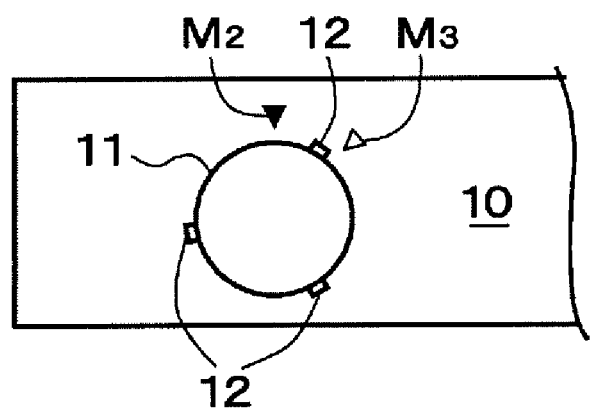
FIG. 11B is a front view of a processor device.

This type of rotating ring 21 enables connection of the connector 15 to the connector receiving part 11 by engaging the cam groove 22C in the engagement hook 12 of the connector receiving part 11 in FIG. 11 and rotating against the resilient force through a predetermined angle to a position $M_3$ from a position at the mark $M_2$. The connector 15 can be removed from the connector receiving part 11 by rotating the rotating ring 21 in the opposite direction. The rotating ring 21 is adapted so that the position of the mark $M_1$ is constantly maintained at a reference position by the resilient force and arranged to facilitate the connection and positional alignment of the connector 15.

A connection port 20a is disposed on the front side of the main body 20 of the connector 15 and a plurality of connector pins (electrical connection members) 23 are disposed in an inner section of the connection port 20a. The main body 20 is divided into a front member 20(F) disposing pins 23 and a rear member 20 (R) mounting the base of the string-like body 17. These members are maintained in a waterproof state by the O ring 24.

On the other hand, the waterproof cap 16 is constituted by an inner cylindrical section 26, a first outer cylindrical section 27 and a second outer cylindrical section 28. All these members are formed from synthetic resin materials (plastic) in order to avoid use of metal. Furthermore an O ring 29 is mounted as a first seal member making close contact with the inner periphery of the connection port 20a, in the groove 26e formed in the outer periphery of the inner cylindrical section 26, that is to say, the outer periphery of the section inserted into the inner side of the connector connection port 20a.

As described above, in the present embodiment, a bayonet-type fixing mechanism is adopted in which an engagement hook 30 is provided in a number of positions (for example, three positions) on a distal end (connection side) of an outer periphery of the first outer cylindrical section 27. The engagement hook 30 is engaged with the cam groove 22C of the cylindrical member 22 on an inner side of the rotating ring 21. In other words, the cylindrical member 22 is mounted integrally with the rotating ring 21 and a cam groove 22C is formed as shown in FIG. 3 on an inner periphery of the cylindrical member 22. In this manner, the entire waterproof cap 16 can be displaced forward and connected and fixed to the connector 15 by engaging the respective engagement hooks 30 with the cam grooves 22C of the cylindrical member 22 of the rotating ring 21 and rotating the waterproof cap 16 through a predetermined angle.

A bayonet-type fixing mechanism allows the disposition of the engagement hooks 30 and the cam grooves 22C to be reversed and the cam groove 22C may be disposed near the waterproof cap 16 and the engagement hook 30 near to the connection 15. Furthermore a threadably engaged type of fixing mechanism can be used as a forward fixing mechanism in which, for example, a male threaded section is provided on an outer periphery of the first outer cylindrical section 27 of the waterproof cap 16 and a female threaded section is provided on an inner side of the cylindrical member 22 of the connector 15.

Figure 4A:
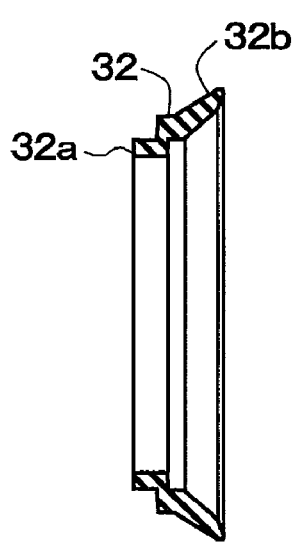
FIGS. 4A and 4B are sectional views showing the structure of a second seal member in this embodiment.

In the first embodiment, a second seal member 32 having a flared shape and making close contact with the front face of the rotating link 21 is mounted on the waterproof cap 16. The second seal member 32 is formed from a resilient rubber member and, as shown in FIG. 4, has a cylindrical base 32a and a flared section 32b, the distal end of which expands in a bell shape (or umbrella shape) from the base 32a. The flared section 32b is formed so that a thickness thereof decreases towards the distal end. As the (diameter of) distal end of the flared section 32b broadens (the contact surface area increases), the flared section 32b is pressed and makes close contact with the front face of the rotating ring 21.

Figure 4B:
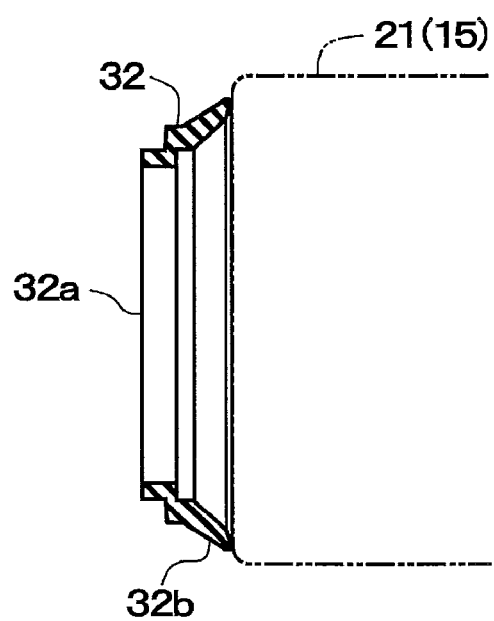

As shown in FIG. 4(B), the diameter of the outer periphery of the flared section 32b of the second seal member 32 is set to a dimension (which may be substantially equal to the outer diameter of the connector 15) which does not exceed the rotating ring 21, that is to say, the outer diameter of the connector 15. In other words, the maximum outer diameter of the second seal member 32 is set to be less than or equal to the outer diameter of the rotating ring 21 (or connector 15) with the distal end of the flared section 32b creating a seal by close contact with the front face of the rotating ring 21. In this manner, in a first embodiment, even when the waterproof cap 16 is mounted, the outer periphery of the connector 15 is not enlarged by the seal section.

Figure 5A:
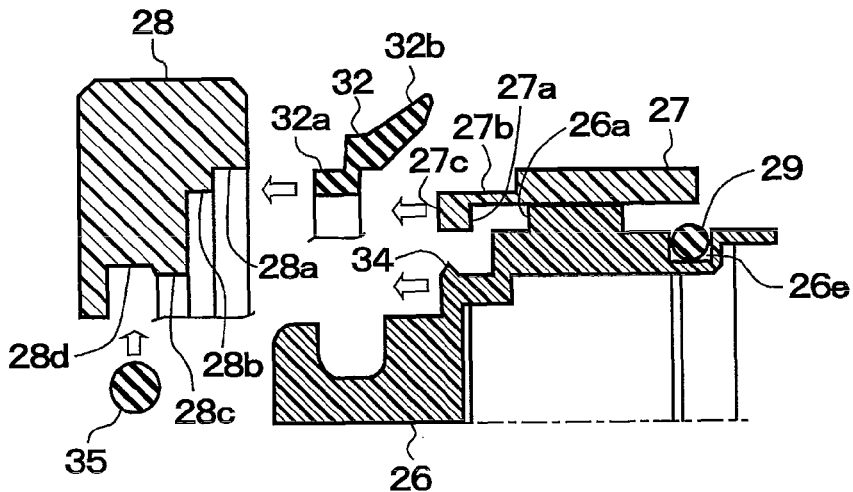
FIG. 5A is an exploded view before mounting of the structure as mounted of the second seal member in this embodiment.

FIGS. 5(A) and (B) show the state before and after the mounting and assembly of the waterproof cap 16. The waterproof cap 16 according to the first embodiment is produced with only press fitting. In other words, a plurality of steps is formed on the rear side (left side of the figure) of the inner cylindrical section 26. In addition, a step is formed on the inner periphery and outer periphery on the rear side of the first outer cylindrical section 27. A first inner peripheral section 28a, a second inner peripheral section 28b, and a third inner peripheral section 28c are formed on an inner side of the second outer cylindrical section 28 and are adapted so that an inner diameter decreases in a backward direction. The front face 26a of the outer peripheral step of the inner cylindrical section 26 abuts with the rear face 27a of the inner peripheral step of the first outer cylindrical section 27.

A space is formed for disposing and sandwiching the cylindrical base 32a of the second seal member 32. The space is formed between the outer peripheral face of the outer peripheral step 27b of the first outer cylindrical section 27 and the inner peripheral face of the first inner peripheral section 28a by placing the front face 27c of the outer peripheral step section 27b of the first outer cylindrical section 27 in abutment with the rear wall face (face with respect to the diameter) of the second inner peripheral section 28b of the second outer cylindrical section 28. A ring-shaped projection 34 is formed on an outer periphery of the step on the inner cylindrical section 26. The projection 34 is fixed by providing a fourth inner peripheral section 28d with an inner diameter larger than the third inner peripheral section 28c on the rear side of the third inner peripheral section 28c and an ring 35 on the fourth inner peripheral section 28d.

Figure 5B:
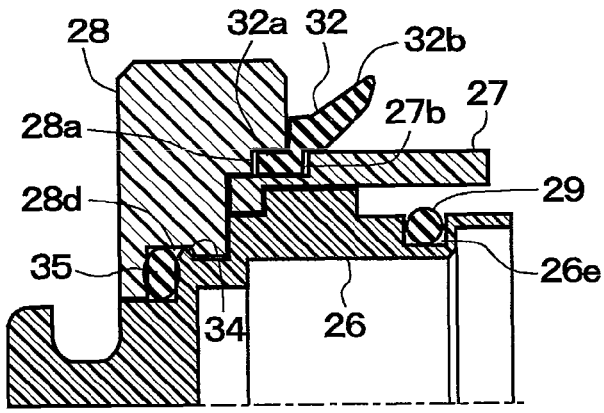
FIG. 5B is a view after assembly of the structure as mounted of the second seal member in this embodiment.

Thus as shown in FIG. 5(B) according to this arrangement, when an O ring 35 is mounted in the fourth inner peripheral section 28d, a base 32a of the second seal member is disposed in a first inner peripheral section 28a of the second outer cylindrical section 28, the first outer cylindrical section 27 and the inner cylindrical section 26 are mounted in order and the inner cylindrical section 26 is pressed (press fitted), the second seal member 32 is mounted by sandwiching between the first inner section 28a of the second outer cylindrical section 28 and the outer step section 27b of the first outer cylindrical section 27 as a result of engagement of the projection 34 with the fourth inner peripheral section 28d. The inner cylindrical section 26 may perform the function of the first outer cylindrical section 27 and the first outer cylindrical section 27 may be omitted.

Figure 6:
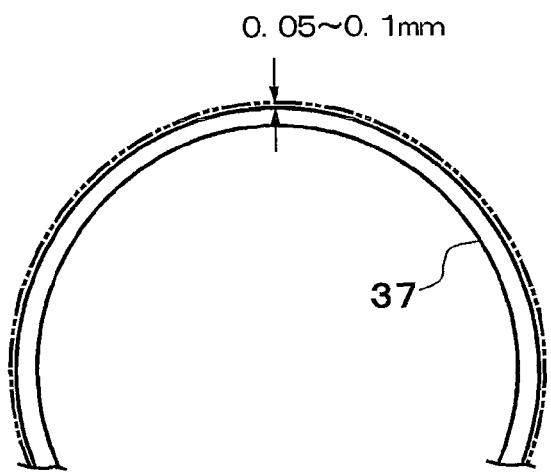
FIG. 6 shows the structure of an O ring in this embodiment.

In the first embodiment, as shown in FIG. 1, a seal member is provided on a rear side (right side of the figure) of the rotating ring 21. In other words, a ring-shaped groove 20e is provided on an outer peripheral face of the distal tip of the rear member 20(R) of the main body 20. An O ring 37 (FIG. 6) is mounted as a third seal member in the groove 20e. The O ring 37 makes close contact with the inner face on the rear side of the rotating ring 21. As shown in FIG. 6, watertight conditions are maintained and an effect on the rotating operation of the rotating ring 21 are avoided by setting the interference of the O ring 37 (the length with respect to a diameter of the cross section circle grasped by the close contact) to the range 0.05-0.1 mm.

Since the first embodiment has the above structure, from the state shown in FIG. 2, when the engagement hook 30 of the waterproof cap 16 is engaged with the cam groove 22C of the inner periphery of the rotating ring 21 (cylindrical member 22) and the waterproof cap 16 is rotated through a predetermined angle, the waterproof cap 16 is displaced forward (drawn into the connector 15) and, as shown in FIG. 1, is mounted on the connector 15. The inner section of the connection port 20a of the connector 15 is placed in a waterproof state by the O ring (first seal member) 29 disposed on the outer periphery of the inner cylindrical section 26.

At the same time, in conjunction with the forward displacement of the waterproof cap 16, the flared section 32b of the second seal member 32 is slightly enlarged and is pressed onto and makes close contact with the front face of the rotating ring 21. In other words, as shown above, since the engagement hooks 30 of the waterproof cap 16 are engaged with the cam grooves 22C of the rotating ring 21, the cam operation displaces the rotating waterproof cap 16 in a direction (the right direction in FIG. 1 and FIG. 2) pressed onto the connector 15. In this manner, close contact of the second seal member 32 with the front face of the rotating ring 21 is ensured and entry of moisture between the rotating ring 21 and the main body 20 from the front side of the connector 15 is prevented. Furthermore since the O ring 37, which acts as a third seal member disposed on an outer periphery of the main body 20(R), makes close contact with the inner peripheral face of the rotating ring 21 on the rear side (cable side) of the connector 15, entry of moisture between the rotating ring 21 and the main body 20 is prevented from the rear side of the connector 15 and as a result waterproof conditions are ensured between the rotating ring 21 and the main body 20.

In this manner, in a first embodiment, corrosion of connector pins 23 and peripheral sections thereto is prevented to a high degree since a seal exists between the rotating ring 21 and the main body 20 in addition to a seal in the section of the connector connection port 20a which results in particular, in prevention of adherence or accumulation of moisture between the rotating ring 21 and the main body 20. As a result, corrosion of electrical connection members in the connector receiving part is also prevented. In the first embodiment, the interference of the ring 27 which acts as a third seal member is set to 0.05 to 0.1 mm and thus good rotating operation of the rotating ring 21 is ensured.

In the connector 15 in this embodiment, as shown in FIG. 11, when the mark $M_1$ provided on an outer periphery of the rotating ring 21 is aligned with a mark $M_2$ on the processor device side, the connector receiving part 11 is inserted into the rotating ring 21. When the rotating ring 21 is rotated up to a connection position mark $M_3$ with the cam grooves 22C engaged with the engagement hooks 12, the connector main body 20 (the connection port 20a thereof) is displaced forward and is connected and fixed to the connector receiving part 11. When the connector 15 is removed from the connector receiving part 11, the rotating ring 21 is returned to the original reference position by the resilient force of a spring. In the conventional example, although moisture entered between the rotating ring 21 and the main body 20, the above structure in this embodiment which has a waterproof cap 16 prevents entry of moisture into the inner side of the rotating ring 21. Furthermore effects resulting from the entry of water into such sections are prevented by the resilient force mechanism of the spring which returns the rotating ring 21 and also avoids reductions in the resilient force of the spring.

Although the first embodiment was described with reference to a rotating ring 21 rotatably provided on an outer periphery of the main body 20, the rotating ring 21 may be substituted by simply affixing an outer covering body. Therefore since the rear side of the outer covering body is fixed in a waterproof state to a member 20(R) on a rear side of the main body, entry and adherence of moisture into the space between the outer covering body and the main body 20 can be prevented by the close contact of the second seal member 32 onto the front face of the outer covering body.

Furthermore in the first embodiment, since the distal end of the flared section 32b of the second seal member 32 is formed in a flared shape which expands into a bell shape and an outer diameter of the flared section 32b has a dimension which does not exceed the outer diameter of the rotating ring 21 (connector 15), even when the waterproof cap 16 is mounted, the outer periphery of the connector 15 is not enlarged by the seal section and thus can be easily handled during sterilization such as washing, disinfection or autoclaving of the endoscope (scope) and can be placed without difficulty in an existing washing vessel or the like. Moreover the waterproof cap itself, as well as the connector with the waterproof cap attached, is slender and compact.

Furthermore as described above, in the first embodiment, the waterproof cap 16 does not use metal and is manufactured using a synthetic resin member or a rubber member. Moreover the second seal member 32 is mounted by simply press fitting the inner cylindrical section 26 through the first outer cylindrical section 27 with respect to the second outer cylindrical section 28 provided with the second seal member 32 without use of an adhesive or fixing screw. Consequently the advantages are obtained that the manufacture of the waterproof cap is facilitated and deterioration of an adhesive or correction of metal sections of the waterproof cap due to washing or sterilization can be suppressed. In other words, although corrosion of metals such as screws, loss of the adhesive effects of adhesives and damage to the waterproof cap tend to occur during sterilization of an endoscope such as washing, disinfection or autoclaving or when placed in high temperature and high humidity and immersed in strong acidic water, such disadvantages can be avoided by the present embodiment.

Figure 7:
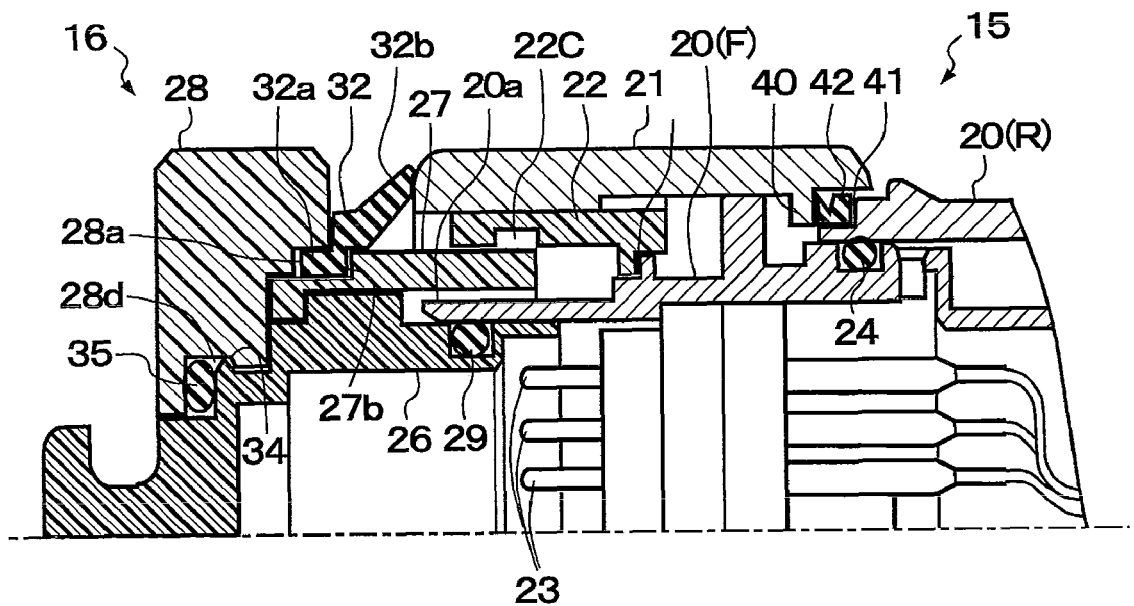
FIG. 7 is a partial sectional view showing the structure of a connector for an endoscope according to the second embodiment of the present invention.

FIG. 7 shows a second embodiment. In the second embodiment, a V ring is used as a third seal member. In other words, the V ring 42 is disposed in the space formed between the rear end of the ring-shaped projection (or may be a ring-shaped step with a decreasing inner diameter) 40 which projects inwardly on an inner periphery of the rear end of the rotating ring 21 and a step 41 having an outer diameter which decreases with respect to the distal end at the outer peripheral distal end of the rear side member 20(R) of the main body. The distal end face of the V ring 42 is mounted to make close contact with the rear end face of the ring-shaped projection 40. In this manner, the V ring 42, in the same manner as the O ring 37, prevents entry of moisture from the rear side of the connector 15 between the rotating ring 21 and main body 20 and, in cooperation with the forward second seal member 32, maintains watertight conditions between the rotating ring 21 and the main body 20.

Figure 8:
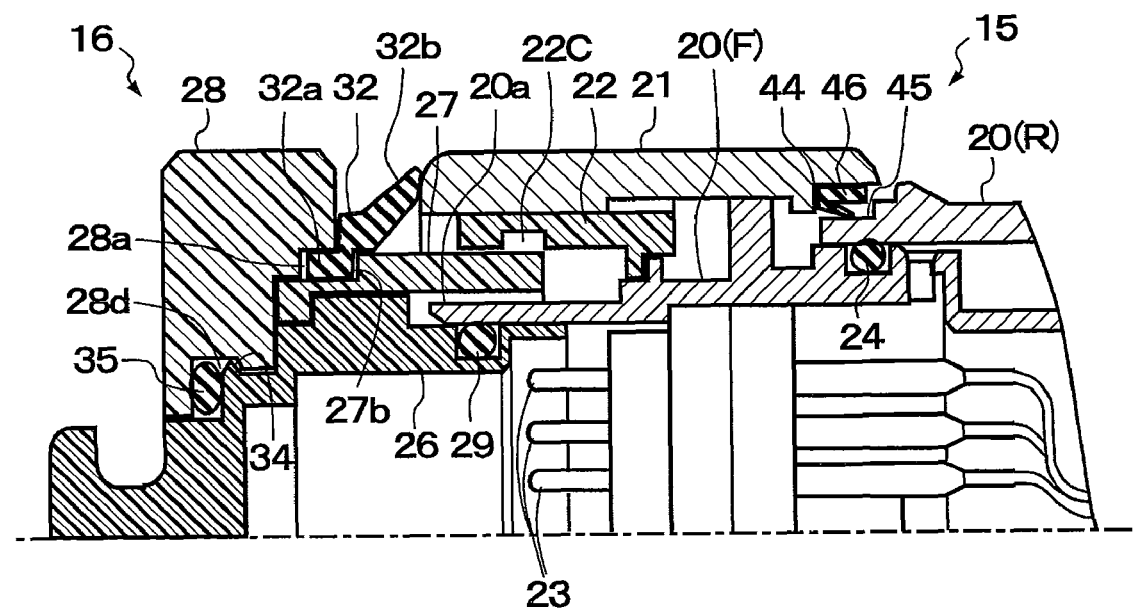
FIG. 8 is a partial sectional view showing the structure of a connector for an endoscope according to a third embodiment of the present invention.

A third embodiment is shown in FIG. 8. The third embodiment uses an oil seal as a third seal member. In other words, an oil seal 46 is disposed in a space between a ring-shaped step 44 having an inner diameter which decreases towards the distal end on the inner periphery of the rear end of the rotating ring 21 and a step 45 having an outer diameter which decreases with respect to the distal end at the outer peripheral distal end of the rear of the main body 20(R). One inner peripheral side of the oil seal 46 is mounted to make close contact with the outer peripheral face of the step 45. In this manner, the oil seal 46, in the same manner as the O ring 37 and the V ring 42, in cooperation with the forward second seal member 32, maintains watertight conditions between the rotating ring 21 and the main body 20. In the second and third embodiments, the interference of the V ring 42 and oil seal 46 is set to a range of 0.05 to 0.1 mm and thus good rotating operation of the rotating ring 21 is ensured.

Figure 9:
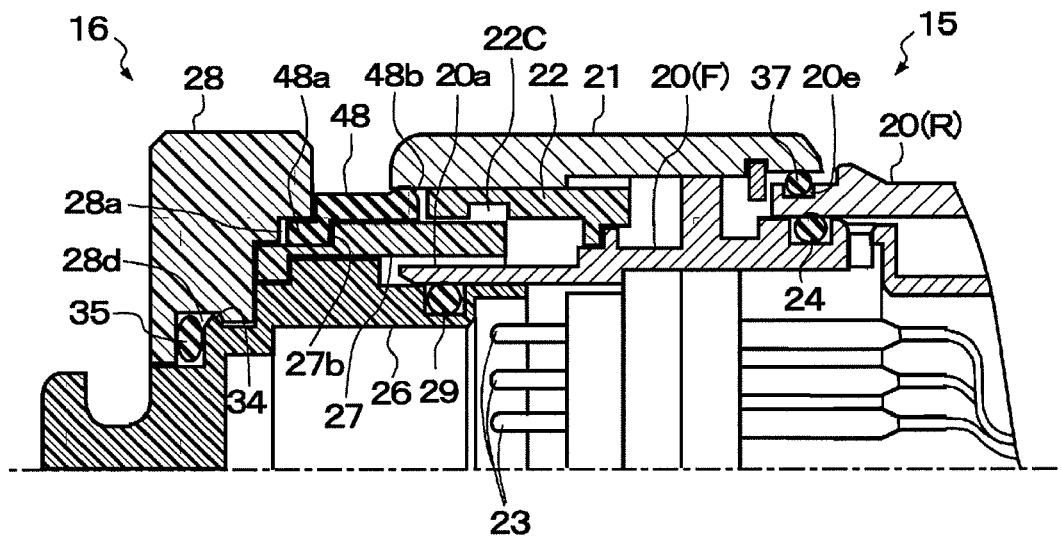
FIG. 9 is a partial sectional view showing the structure of a connector for an endoscope according to a fourth embodiment of the present invention.
Figure 10:
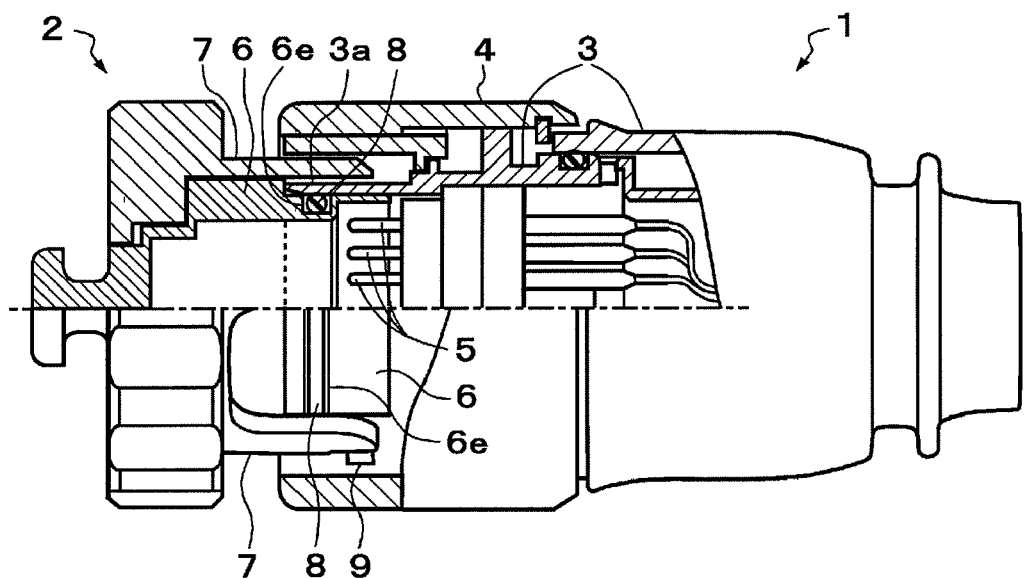
FIG. 10 is a partial sectional view showing the structure of a conventional connector for an endoscope.

FIG. 9 shows a fourth embodiment of the present invention. In the fourth embodiment, the second seal member is disposed in close contact with the inner peripheral face of the rotating ring. As shown in FIG. 9, the second seal member 48 of the waterproof cap 16 integrally forms a cylindrical main body on a cylindrical base 48a, the main body having a diameter which is greater than that of the base. A ring-shaped projection 48b is provided on an outer periphery of a distal end of the main body. Thus in the same manner as the first embodiment, the base 48a is disposed in the first inner peripheral section 28a and the first outer cylindrical section 27 and the inner cylindrical section 26 are mounted in order. By press fitting the inner cylindrical section 26, the second seal member 48 is mounted by sandwiching between the first inner section 28a of the second outer cylindrical section 28 and the outer step section 27b of the first outer cylindrical section 27 as a result of engagement of the projection 34 with the fourth inner peripheral section 28d.

When the waterproof cap 16 is mounted, the projection 48b of the second seal member 48 makes close contact with the inner periphery of the rotating ring 21 and thus moisture is prevented from entering between the rotating ring 21 and the main body 20 from the front side of the connector 15 and, in cooperation with the O ring 37 on the rear side of the connector 15, a watertight condition is maintained between the rotating ring 21 and the main body 20.

In the fourth embodiment, since the outer periphery of the second seal member 48 is formed with a dimension which does not exceed the outer diameter of the rotating ring 21 (connector 15), even when the waterproof cap 16 is mounted, the outer periphery of the connector 15 is not enlarged by the seal section and thus can be easily handled during sterilization such as washing, disinfection or autoclaving of the endoscope (scope).

The fourth embodiment can be applied to the arrangement of substituting the rotating ring 21 by simply affixing an outer covering body. If the projection 48b of the second seal member 48 makes close contact with the inner peripheral face of the outer covering body, entry of moisture into the space between the outer covering body and the main body 20 can be prevented.

| Description of Symbols | | | |
|---|---|---|---|
| 1, 15 | CONNECTOR | 2, 16 | CAP |
| 3, 20 | MAIN BODY | 4, 21 | ROTATING RING |
| 3a, 20a | CONNECTION PORT | | |
| 20e, 26e | GROOVE | 22C | CAM GROOVE |
| 24, 35 | O RING | 29 | O RING (FIRST SEAL MEMBER) |
| 26 | INNER CYLINDRICAL SECTION | | |
| 27 | FIRST OUTER CYLINDRICAL SECTION | | |
| 28 | SECOND OUTER CYLINDRICAL SECTION | | |
| 28a-28d | FIRST - FORTH INNER PERIPHERAL SECTION | | |
| 32, 48 | SECOND SEAL MEMBER | | |
| 32a, 48a | BASE | 32b | FLARED SECTION |
| 37 | O RING (THIRD SEAL MEMBER) | | |
| 40, 48b | PROJECTION | 41, 44, 45 | STEP |
| 42 | V RING (THIRD SEAL MEMBER) | | |
| 46 | OIL SEAL (THIRD SEAL MEMBER) | | |

CITATION LIST

Patent Document 1: JP-A-6-133919
Patent Document 2: JP-A-2000-340290
Patent Document 3: JP-A-2005-278944
Patent Document 4: JP-A-2001-204681
Patent Document 5: JP-A-2005-192772

What is claimed is:

1. A connector for an endoscope comprising:
   a connection port for a connector having an electrical connection member disposed therein;
   an outer member disposed on an outer periphery of the connection port; and
   a waterproof cap mounted on the connection port of the connector; wherein
      the waterproof cap comprises a first seal member providing waterproof characteristics by making close contact with an inner peripheral face of the connection port and a second seal member providing waterproof characteristics by making close contact with the front face of the outer member, and
      the outer member is a rotating ring rotatably disposed on an outer peripheral side of the connection port and rotated to fix the connector into a connector receiving part, and a third seal member maintaining watertight conditions is provided between a rear end of the rotating ring and the connector main body, and the second seal member of the waterproof cap is disposed in close contact with the front face of the rotating ring.

2. The connector for an endoscope according to claim 1, wherein the third seal member comprises an O ring, a V ring or an oil seal.

3. A connector for an endoscope comprising:
   a connection port for a connector having electrical connection member disposed therein;
   an outer member disposed on an outer periphery of the connection port; and
   a waterproof cap mounted on the connection port of the connector; wherein
      the waterproof cap comprises a first seal member providing waterproof characteristics by making close contact with an inner peripheral face of the connection port and a second seal member comprising a seal body of a size not exceeding the outer periphery of the outer member and providing waterproof characteristics by making close contact with the front face of the outer member, and
      the outer member is a rotating ring rotatably disposed on an outer side of the connection port and rotated to fix the connector into a connector receiving part, and a third seal member maintaining watertight conditions is provided between a rear end of the rotating ring and the connector main body, and the second seal member of the waterproof cap is disposed in close contact with the rotating ring.

4. The connector for an endoscope according to claim 3, wherein the second seal member makes close contact with the inner peripheral face of the outer member.

5. The connector for an endoscope according to claim 3, wherein the third seal member comprises an O ring, a V ring or an oil seal.

6. A connector for an endoscope comprising:
   a connection port for a connector having electrical connection member disposed therein;
   a waterproof cap mounted on the connection port of the connector;

a waterproof seal member for the connector comprising resilient rubber;

a first member and a second member formed from a synthetic resin material, the first member and second member are constituted by at least two members forming the waterproof cap by connection via press fitting, and forming a space into which a base of the seal member is sandwiched during press fitting and connection;

a first seal member of the waterproof cap providing waterproof characteristics by making close contact with an inner peripheral face of the connection port; and a second seal member of the waterproof cap providing waterproof characteristics by making close contact with an outer member disposed on an outer side of the connection port, wherein the waterproof seal member is mounted on the waterproof cap by sandwiching the seal member between the first member and second member and press fitting and connection of the first member and second member, the outer member is a rotating ring rotatably disposed on an outer side of the connection port and rotated to fix the connector into a connector receiving part, and a third seal member maintaining watertight conditions is provided between a rear end of the rotating ring and the connector main body, and the second seal member of the waterproof cap is disposed in close contact with the rotating ring.

* * * * *